US012599306B2

(12) United States Patent
Wu et al.

(10) Patent No.: US 12,599,306 B2
(45) Date of Patent: Apr. 14, 2026

(54) PUPIL DYNAMICS, PHYSIOLOGY, AND PERFORMANCE FOR ESTIMATING COMPETENCY IN SITUATIONAL AWARENESS

(71) Applicant: Rockwell Collins, Inc., Cedar Rapids, IA (US)

(72) Inventors: Peggy Wu, Ellicott City, MD (US); Brigid A. Blakeslee, Hamden, CT (US); Andrew Radlbeck, South Glastonbury, CT (US); Ganesh Sundaramoorthi, Duluth, GA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 374 days.

(21) Appl. No.: 18/216,825

(22) Filed: Jun. 30, 2023

(65) Prior Publication Data
US 2025/0000372 A1 Jan. 2, 2025

(51) Int. Cl.
| | |
|---|---|
| *A61B 5/0205* | (2006.01) |
| *A61B 5/024* | (2006.01) |
| *A61B 5/16* | (2006.01) |
| *B64D 45/00* | (2006.01) |
| *G06F 3/01* | (2006.01) |
| *G06V 10/82* | (2022.01) |
(Continued)

(52) U.S. Cl.
CPC ............ *A61B 5/0205* (2013.01); *G06V 20/44* (2022.01); *G06V 40/18* (2022.01); *A61B 5/024* (2013.01)

(58) Field of Classification Search
CPC ......... A61B 5/0205; A61B 5/024; A61B 5/16; A61B 5/163; A61B 5/165; G06V 20/44; G06V 40/18; G06V 10/82; B64D 45/0053; B64D 45/0056; G06F 3/013
See application file for complete search history.

(56) References Cited

U.S. PATENT DOCUMENTS

| | | | |
|---|---|---|---|
| 9,298,985 B2 | 3/2016 | Krueger | |
| 9,451,899 B2 | 9/2016 | Ritchey et al. | |
(Continued)

FOREIGN PATENT DOCUMENTS

| | | |
|---|---|---|
| WO | 2007102053 A2 | 9/2007 |
| WO | 2022224173 A1 | 10/2022 |

OTHER PUBLICATIONS

European Search Report received in EP Application No. 24185817.4, Nov. 26, 2024, 8 pages.

*Primary Examiner* — Justin Xu
(74) *Attorney, Agent, or Firm* — Suiter Swantz IP

(57) ABSTRACT

A computer system records eye tracking data and identifies movements in the eye tracking data to determine gaze and pupil dynamics. Eye tracking data is correlated with physiological data including heart rate. The system looks at the heart rate of the operator in real time to evaluate whether they exhibit an anticipatory response to switch attention. The system differentiates between behaviors that are cognitively initiated as opposed to triggered by the environment. The system correlates eye tracking data and physiological data with previously identified knowledge about the training scenario to assess whether the operator is able to direct attention to the right stimuli based on task needs. The system examines whether there is follow through behavior of shifting gaze to specific instruments as defined by the current task.

16 Claims, 3 Drawing Sheets

(51) Int. Cl.
  *G06V 20/40*          (2022.01)
  *G06V 40/18*          (2022.01)

(56)                References Cited

U.S. PATENT DOCUMENTS 10,102,773  B2    10/2018   Towers et al.
2020/0383621  A1*   12/2020   Cuestas Rodriguez ..  A61B 5/11
2022/0306143  A1     9/2022   Samani et al.
2023/0093444  A1     3/2023   Zander et al.

* cited by examiner

100

108

110

112

102

114

106

104

200  RECEIVE BIOMETRIC DATA

202  CONTINUOUSLY LOG BIOMETRIC DATA

204  ANALYZE BIOMETRIC DATA FOR COGNITIVE INITIATION

206  COMPARE THE BIOMETRIC DATA TO THE TASK SPECIFIC PROFILE

PUPIL DYNAMICS, PHYSIOLOGY, AND PERFORMANCE FOR ESTIMATING COMPETENCY IN SITUATIONAL AWARENESS

BACKGROUND

The increasing expense of training for complicated tasks, such as pilot training, coupled with rapid advancements in computer modeling and simulation capabilities are fostering substantial growth in the use of simulation-based training technologies. Additionally, low-cost, commercial-off-the shelf (COTS) technologies are beginning to supplant custom simulation environments. However, training in general, and training via simulated environments, has substantial limitations.

Situation awareness is difficult to measure. Currently, measuring one's situation awareness requires pausing training or simulation exercises, and administering self-report surveys. This process is time consuming, and can take a trainee out of a simulation, affecting the realism of the experience. However, assessing the operator's level of situation awareness in situ is important for assessing their competency and readiness.

Consequently, it would be advantageous if an apparatus existed that is suitable for monitoring a trainee's situational awareness during a training operation.

SUMMARY

In one aspect, embodiments of the inventive concepts disclosed herein are directed to a computer system that records eye tracking data. The system identifies movements in the eye tracking data to determine gaze and pupil dynamics. Eye tracking data is correlated with physiological data including heart rate. The system looks at the heart rate of the operator in real time to evaluate whether they exhibit an anticipatory response to switch attention. The system differentiates between behaviors that are cognitively initiated as opposed to triggered by the environment.

In a further aspect, the system correlates eye tracking data and physiological data with previously identified knowledge about the training scenario to assess whether the operator is able to direct attention to the right stimuli based on task needs.

In a further aspect, the system examines whether there is follow through behavior of shifting gaze to specific instruments as defined by the current task.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which.

DETAILED DESCRIPTION

Figure 1:
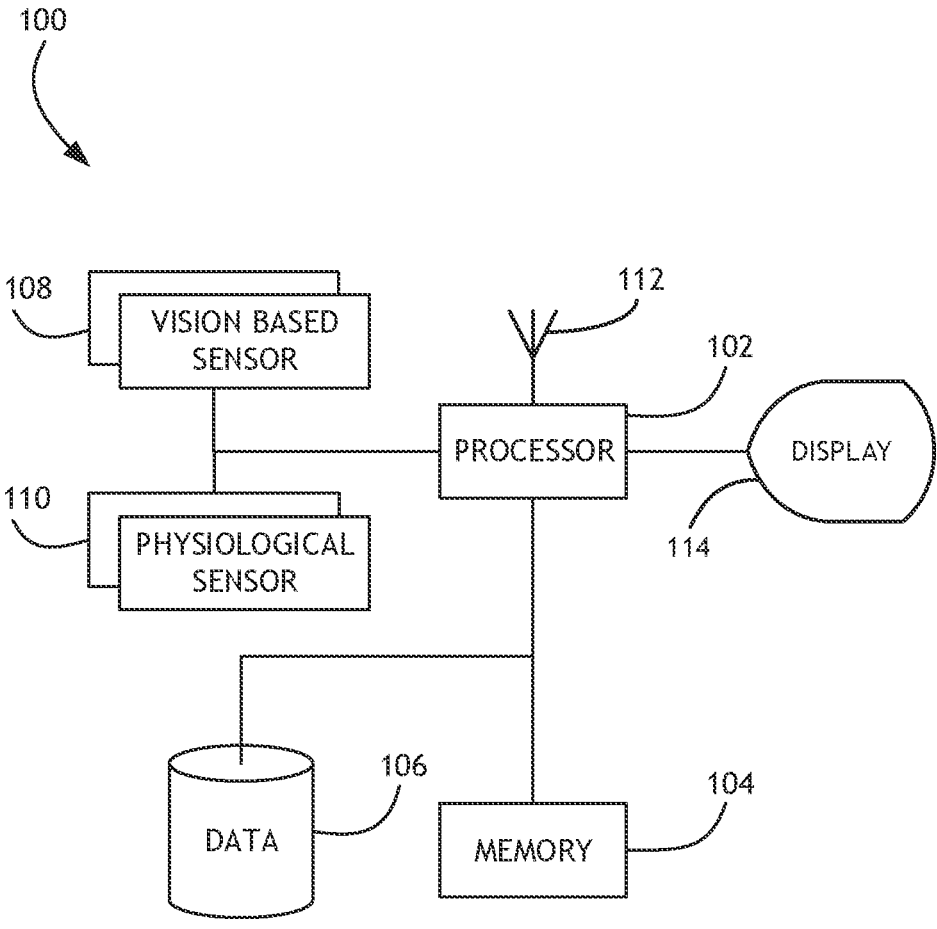
FIG. 1 shows a block diagram of a system suitable for implementing embodiments of the incentive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., $1$, $1a$, $1b$). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a" and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to a computer system that records eye tracking data. The system identifies movements in the eye tracking data to determine gaze and pupil dynamics. Eye tracking data is correlated with physiological data including heart rate. The system looks at the heart rate of the operator in real time to evaluate whether they exhibit an anticipatory response to switch attention. The system differentiates between behaviors that are cognitively initiated as opposed to triggered by the environment. The system correlates eye tracking data and physiological data with previously identified knowledge about the training scenario to assess whether the operator is able to direct attention to the right stimuli based on task needs. The system examines whether there is follow through behavior of shifting gaze to specific instruments as defined by the current task.

Referring to FIG. 1, a block diagram of a system 100 suitable for implementing embodiments of the incentive concepts disclosed herein is shown. The system 100 includes a processor 102, memory 104 in data communication with the processor 102 for storing processor executable code, one or more eye tracking sensors/cameras 108 for receiving eye tracking data stream, and one or more physiological sensors 110, including at least one heart rate monitor. Physiological sensors 110 may include devices such as an electroencephalograph (EEG), an electrocardiogramalvanic skin response sensor (GSR), pulse sensor, or any other such biometric data sensing device.

In at least one embodiment, the eye tracking sensors 108 record eye movement/gaze of a pilot and eye lid position. The processor executable code configures the processor 102 to continuously log the eye tracking data in a data storage element 106. The processor 102 analyzes the eye tracking data to identify gaze and pupil dynamics (e.g., pupil response and changes over time). The processor 102 also receives physiological data from one or more physiological sensors 110. The physiological data may include, but is not limited to the user's heart rate. In at least one embodiment, the processor 102 correlates eye tracking data (including at least gaze and pupil dynamics) with physiological data (including at least heart rate).

In at least one embodiment, eye tracking data and physiological data are correlated with discreet portions of a training scenario, and/or specific stimuli such as instrument readings, alerts, or the like. The processor 102 determines whether the eye tracking data and physiological data correspond to predetermined behaviors indicative of volitional attention shifting. In some instances, stimuli may induce an involuntary shift in gaze. Embodiments of the present disclosure are directed toward identifying an anticipatory response (e.g., gaze shift and pupil changes) correlated to subsequent actions generally anticipated in response to a given scenario. For example, for some stimuli (e.g., an alert message), a user should anticipate a need for certain information from the available instruments at some point in the future. The processor 102 may determine if the user begins shifting gaze to those instruments within some threshold time. This provides a method to differentiated between behaviors that are cognitively initiated as opposed to triggered by the environment.

In at least one embodiment, the processor 102 may compare the eye tracking and physiological data to stored profiles. Such profiles may be specific to the user and indicate a user specific minimum threshold. Alternatively, or in addition, the profiles may represent some standard minimum response.

In at least one embodiment, the processor 102 may alert a remote party such as ground control personnel via a wireless communication device 112. Alternatively, or in addition, the processor 102 may render the determination of cognitively initiated responses on a display 114. For example, in a training scenario, an instructor may continuously monitor cognitively initiated responses (as compared to stimuli triggered responses) on the display 114.

In at least one embodiment, the processor 102 transfers the stored eye tracking data and other correlated system and task data to an offline storage device for later analysis and correlation to historic data and other outside factors such as crew rest, crew sleet rhythms, flight schedules, etc. Such transfer may be in real time via the wireless communication device 112.

Figure 2:
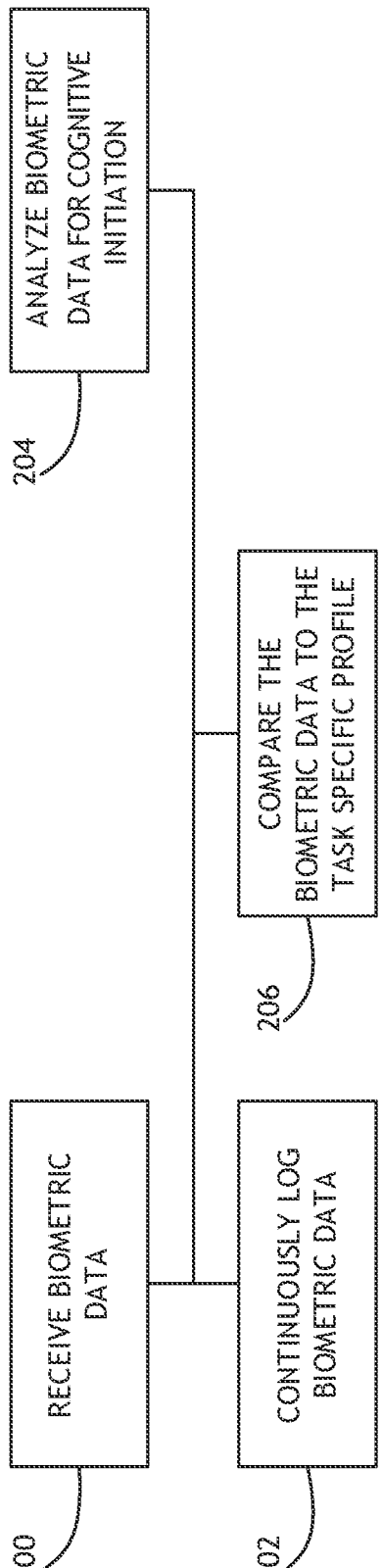
FIG. 2 shows a flowchart of an exemplary embodiment of the inventive concepts disclosed herein.

Referring to FIG. 2, a flowchart of an exemplary embodiment of the inventive concepts disclosed herein is shown. A computer system implementing embodiments of the inventive concepts disclosed herein receives 200 an image stream corresponding to eye tracking data from one or more vision-based sensors and physiological data, including at least heart rate data, from one or more physiological sensors. The eye tracking data and physiological data are continuously logged 202 and correlated to a specific flight task or an individual duty schedule of the user/pilot.

In at least one embodiment, the eye tracking data is analyzed 204 to characterize gaze and pupil dynamics as cognitively initiated or stimuli triggered. Such analysis 204 may include processing via machine learning, neural network algorithms. Cognitive initiation may be characterized by timing; for example, gaze shift and/or pupil dynamics that are stimuli triggered may be generally faster and more cursory than cognitively initiated gaze shifts.

In at least one embodiment, gaze and pupil dynamics may be analyzed 204 along with physiological data such as heart rate. Gaze and pupil dynamics correlated to certain heart rate ranges, and in the context of specific stimuli, may indicate cognitively initiated responses as opposed to stimuli triggered responses. In at least one embodiment, small involuntary eye movements (and potentially eye lid movement/position) may be identified and used to characterize the gaze and pupil dynamics.

The determination of cognitive initiation may be ex post facto. In at least one embodiment, cognitively initiated responses may be associated with a set of anticipatory responses. If the set of anticipatory responses is later identified, the initial response may be characterized as cognitively initiated.

In at least one embodiment, eye tracking data and physiological data may be compared 206 to task or user specific profiles. The task or user specific profiles may define a minimum characterization of cognitively initiation, either based on previously observed responses of known experts, or based on previously observed responses of the user.

Embodiments of the inventive concepts disclosed herein are critical to enabling reduced crew or single pilot operations, and will provide independent measures necessary to facilitate reduced crew in the cockpit by providing a means to identify when crew members are unable to continue safe flight and notify relief crew or activate automation. Furthermore, a training application may utilize embodiments of the inventive concepts to compare the small involuntary eye movements of a pilot-in-training to previously characterized professional pilot data patterns. Improved methods of assessing an operator's ability to acquire and maintain situation awareness is important for training. As such, it can serve as enabling technologies for single pilot operations or reduced crew operations.

Figure 3:
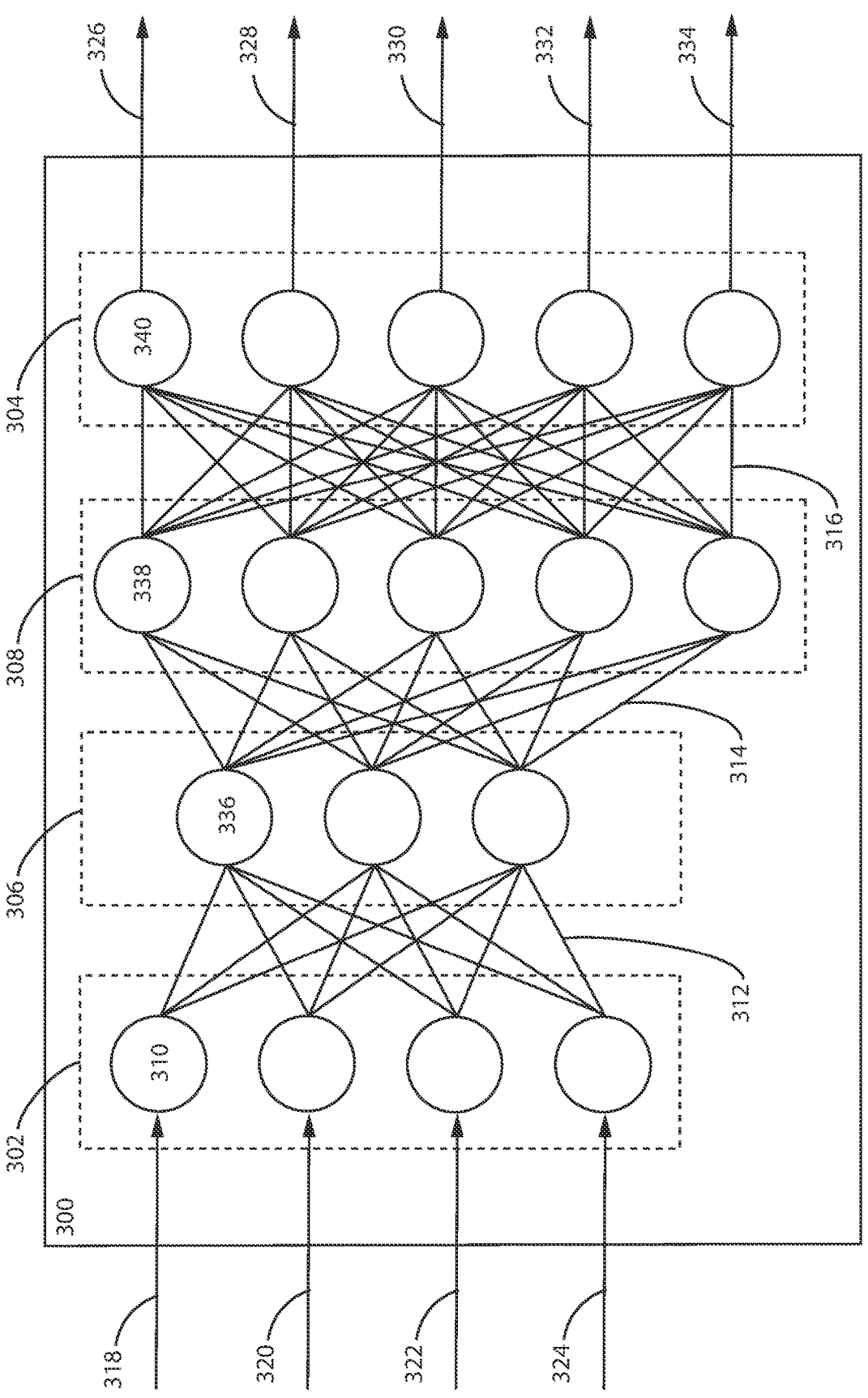
FIG. 3 shows a block diagram of a neural network according an exemplary embodiment of the inventive concepts disclosed herein.

Referring to FIG. 3, a block diagram of a neural network 300 according an exemplary embodiment of the inventive concepts disclosed herein is shown. The neural network 300 comprises an input layer 302 that receives external inputs (including physiological signals, such as EEG, ECG, and GSR, eye tracking data, and potentially user or task specific profiles), and output layer 304, and a plurality of internal layers 306, 308. Each layer comprises a plurality of neurons or nodes 310, 336, 338, 340. In the input layer 302, each node 310 receives one or more inputs 318, 320, 322, 324 corresponding to a digital signal and produces an output 312 based on an activation function unique to each node 310 in the input layer 302. An activation function may be a Hyperbolic tangent function, a linear output function, and/or a logistic function, or some combination thereof, and different nodes 310, 336, 338, 340 may utilize different types of activation functions. In at least one embodiment, such activation function comprises the sum of each input multiplied by a synaptic weight. The output 312 may comprise a real value with a defined range or a Boolean value if the activation function surpasses a defined threshold. Such ranges and thresholds may be defined during a training process. Furthermore, the synaptic weights are determined during the training process.

Outputs 312 from each of the nodes 310 in the input layer 302 are passed to each node 336 in a first intermediate layer 306. The process continues through any number of intermediate layers 306, 308 with each intermediate layer node 336, 338 having a unique set of synaptic weights corresponding to each input 312, 314 from the previous intermediate layer 306, 308. It is envisioned that certain intermediate layer nodes 336, 338 may produce a real value with a range while other intermediated layer nodes 336, 338 may produce a Boolean value. Furthermore, it is envisioned that certain intermediate layer nodes 336, 338 may utilize a weighted input summation methodology while others utilize a weighted input product methodology. It is further envisioned that synaptic weight may correspond to bit shifting of the corresponding inputs 312, 314, 316.

An output layer 304 including one or more output nodes 340 receives the outputs 316 from each of the nodes 338 in the previous intermediate layer 308. Each output node 340 produces a final output 326, 328, 330, 332, 334 via processing the previous layer inputs 316, the final output 326, 328, 330, 332, 334 corresponding to a characterization of a set of physiological data as either cognitively initiated or stimuli triggered. Such outputs may comprise separate components of an interleaved input signal, bits for delivery to a register, or other digital output based on an input signal and DSP algorithm.

In at least one embodiment, each node 310, 336, 338, 340 in any layer 302, 306, 308, 304 may include a node weight to boost the output value of that node 310, 336, 338, 340 independent of the weighting applied to the output of that node 310, 336, 338, 340 in subsequent layers 304, 306, 308. It may be appreciated that certain synaptic weights may be zero to effectively isolate a node 310, 336, 338, 340 from an input 312, 314, 316, from one or more nodes 310, 336, 338 in a previous layer, or an initial input 318, 320, 322, 324.

In at least one embodiment, the number of processing layers 302, 304, 306, 308 may be constrained at a design phase based on a desired data throughput rate. Furthermore, multiple processors and multiple processing threads may facilitate simultaneous calculations of nodes 310, 336, 338, 340 within each processing layers 302, 304, 306, 308.

Layers 302, 304, 306, 308 may be organized in a feed forward architecture where nodes 310, 336, 338, 340 only receive inputs from the previous layer 302, 304, 306 and deliver outputs only to the immediately subsequent layer 304, 306, 308, or a recurrent architecture, or some combination thereof.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A computer apparatus comprising:
at least one eye tracking camera configured to capture image frames including pupil size, blink properties, eyelid position, and eye movement at a defined sampling rate;
at least one physiological sensor comprising at least a heart-rate monitor configured to generate a time-synchronized physiological data stream; and
at least one processor in data communication with a memory storing processor executable code; and
wherein the processor executable code configures the at least one processor to:
receive an image stream from the at least one eye tracking camera;
receive physiological data from the one or more physiological data recording devices, including at least a heart rate;
identify gaze and pupil dynamics, including pupil response, over time from the image stream;
identify involuntary eye movements and involuntary eye lid movements;
correlate the physiological data with the gaze and pupil dynamics;
correlate the gaze and pupil dynamics, and the physiological data with one or more stimuli;
determine whether the gaze and pupil dynamics, and physiological data correspond to predetermined behaviors indicative of volitional attention shifting;
determine if a user begins shifting gaze to one or more instrument readings or alert messages corresponding to the volitional attention shifting within some threshold time;
characterize the gaze and pupil dynamics as either cognitively initiated or stimuli triggered with reference to the gaze and pupil dynamics, physiological data, involuntary eye movements, and involuntary eye lid movements; and
activate automation when the characterization indicates a user is unable to continue safe flight.

2. The computer apparatus of claim 1, wherein:
the processor executable code further configures the at least one processor to receive a task or user specific profile of gaze, pupil dynamics, and physiological data; and
characterizing the gaze and pupil dynamics includes reference to the task or user specific profile.

3. The computer apparatus of claim 1, further comprising a data storage element in data communication with the at least one processor, wherein the processor executable code further configures the at least one processor to continuously store the gaze and pupil dynamics in the data storage element.

4. The computer apparatus of claim 3, wherein:
the processor executable code further configures the at least one processor to:
identify subsequent user-initiated responses; and
correlate the subsequent responses to the stored gaze and pupil dynamics; and
characterizing the gaze and pupil dynamics includes reference to the identified subsequent user-initiated responses to determine if the user-initiated responses correspond to anticipatory responses.

5. The computer apparatus of claim 3, wherein the processor executable code further configures the at least one processor to:
analyze the stored gaze and pupil dynamics over time to identify a user specific profile of a user; and
subsequently compare the gaze and pupil dynamics to the user specific profile.

6. The computer apparatus of claim 1, wherein the processor executable code further configures the at least one processor as a machine learning neural network.

7. A method comprising:
receiving an image stream from at least one eye tracking camera;
receiving physiological data from one or more physiological data recording devices, including at least a heart rate;
identifying gaze and pupil dynamics, including pupil response, over time from the image stream;
identifying involuntary eye movements and involuntary eye lid movements;
correlating the physiological data with the gaze and pupil dynamics;
correlating the gaze and pupil dynamics, and the physiological data with one or more stimuli;
determining whether the gaze and pupil dynamics, and physiological data correspond to predetermined behaviors indicative of volitional attention shifting;
determining if a user begins shifting gaze to one or more instrument readings or alerts corresponding to the volitional attention shifting within some threshold time;
characterizing the gaze and pupil dynamics as either cognitively initiated or stimuli triggered with reference to the gaze and pupil dynamics, physiological data, involuntary eye movements, and involuntary eye lid movements; and
activating automation when the characterization indicates a user is unable to continue safe flight.

8. The method of claim 7, further comprising receiving a task or user specific profile of gaze, pupil dynamics, and physiological data, wherein characterizing the gaze and pupil dynamics includes reference to the task or user specific profile.

9. The method of claim 7, further comprising continuously storing the gaze and pupil dynamics in a data storage element.

10. The method of claim 9, further comprising:
identifying subsequent user-initiated responses; and
correlating the subsequent responses to the stored gaze and pupil dynamics,
wherein characterizing the gaze and pupil dynamics includes reference to the identified subsequent user-initiated responses to determine if the user-initiated responses correspond to anticipatory responses.

11. The method of claim 9, further comprising:
analyzing the stored gaze and pupil dynamics over time to identify a user specific profile of a user; and
subsequently comparing the gaze and pupil dynamics to the user specific profile.

12. A simulator comprising:
at least one eye tracking camera configured to capture image frames including pupil size, blink properties, eyelid position, and eye movement at a defined sampling rate;
at least one physiological sensor comprising at least a heart-rate monitor configured to generate a time-synchronized physiological data stream; and
at least one processor in data communication with a memory storing processor executable code; and
wherein the processor executable code configures the at least one processor to:
receive an image stream from the at least one eye tracking camera;
receive physiological data from the one or more physiological data recording devices, including at least a heart rate;
identify gaze and pupil dynamics, including pupil response, over time from the image stream;
identify involuntary eye movements and involuntary eye lid movements;
correlate the physiological data with the gaze and pupil dynamics;
correlate the gaze and pupil dynamics, and the physiological data with one or more stimuli;
determine whether the gaze and pupil dynamics, and physiological data correspond to predetermined behaviors indicative of volitional attention shifting;
determine if a user begins shifting gaze to one or more instrument readings or alerts corresponding to the volitional attention shifting within some threshold time;
characterize the gaze and pupil dynamics as either cognitively initiated or stimuli triggered with reference to the gaze and pupil dynamics, physiological data, involuntary eye movements, and involuntary eye lid movements; and
activate automation when the characterization indicates a user is unable to continue safe flight.

13. The simulator of claim 12, wherein:
the processor executable code further configures the at least one processor to receive a task or user specific profile of gaze, pupil dynamics, and physiological data; and
characterizing the gaze and pupil dynamics includes reference to the task or user specific profile.

14. The simulator of claim 12, further comprising a data storage element in data communication with the at least one processor, wherein the processor executable code further configures the at least one processor to continuously store the gaze and pupil dynamics in the data storage element.

15. The simulator of claim 14, wherein:
the processor executable code further configures the at least one processor to:
identify subsequent user-initiated responses; and
correlate the subsequent responses to the stored gaze and pupil dynamics; and
characterizing the gaze and pupil dynamics includes reference to the identified subsequent user-initiated responses to determine if the user-initiated responses correspond to anticipatory responses.

16. The simulator of claim 14, wherein the processor executable code further configures the at least one processor to:

analyze the stored gaze and pupil dynamics over time to identify a user specific profile of a user; and subsequently compare the gaze and pupil dynamics to the user specific profile.

<div align="center">*   *   *   *   *</div>